US00PP11785P2

(12) United States Plant Patent
Berres

(10) Patent No.: US PP11,785 P2
(45) Date of Patent: Feb. 20, 2001

(54) OSTEOSPERMUM PLANT NAMED 'SIRIUS'

(75) Inventor: Marcus Berres, Bingen (DE)

(73) Assignee: Innovaplant GmbH & Co. KG, Gensingen (DE)

( * ) Notice: Under 35 U.S.C. 154(b), the term of this patent shall be extended for 0 days.

(21) Appl. No.: 09/291,108

(22) Filed: Apr. 14, 1999

(51) Int. Cl.[7] ..... A01H 5/00

(52) U.S. Cl. ..... Plt./360

(58) Field of Search ..... Plt./360

(56) References Cited

PUBLICATIONS

UPOV CD–ROM, PBR 952508, Osteospermum designated Sirius, 1996.*

* cited by examiner

*Primary Examiner*—Bruce R. Campell
*Assistant Examiner*—Melissa L. Kimball
(74) *Attorney, Agent, or Firm*—C. A. Whealy

(57) ABSTRACT

A distinct cultivar of Osteospermum plant named 'Sirius', characterized by its mostly upright plant habit; freely branching; good vigor; early and continuous flowering; large inflorescences with intense dark purple ray florets; and good summer performance.

1 Drawing Sheet

BACKGROUND OF THE INVENTION

The present invention relates to a new and distinct cultivar of Osteospermum plant, botanically known as *Osteospermum ecklonis* and referred to by the cultivar name Sirius.

The new cultivar is a product of a planned breeding program conducted by the Inventor in Gensingen, Germany. The objective of the breeding program was to create new Osteospermum cultivars with early flowering, interesting inflorescence colors and improved summer performance.

The new cultivar originated from a cross made by the Inventor of the *Osteospermum ecklonis* cultivar Sunny Lady, disclosed in U.S. Plant Pat. No. 10,353, as the female, or seed, parent and an unnamed proprietary selection of *Osteospermum ecklonis* as the male, or pollen, parent. The new Osteospermum was selected by the Inventor as a flowering plant within the progeny of this cross in a controlled environment in Gensingen, Germany, in the summer of 1994.

Plants of the new cultivar are different from plants of the female parent, the cultivar Sunny Lady, in the following characteristics:

1. Plants of the new Osteospermum are more vigorous than plants of the cultivar Sunny Lady.

2. Plants of the new Osteospermum have more durable foliage than plants of the cultivar Sunny Lady.

3. Plants of the new Osteospermum have larger inflorescences than plants of the cultivar Sunny Lady.

4. Ray floret color of the new Osteospermum is much more intense than ray floret color of the cultivar Sunny Lady.

5. Plants of the new Osteospermum have longer peduncles than plants of the cultivar Sunny Lady.

Plants of the new cultivar are different from plants of the male parent, the unnamed proprietary selection of *Osteospermum ecklonis,* in the following characteristics:

1. Plants of the new Osteospermum are more compact than plants of the unnamed proprietary selection of *Osteospermum ecklonis.*

2. Plants of the new Osteospermum have larger inflorescences than plants of the unnamed proprietary selection of *Osteospermum ecklonis.*

3. Plants of the new Osteospermum have shorter peduncles than plants of the unnamed proprietary selection of *Osteospermum ecklonis.*

Asexual propagation of the new cultivar by terminal cuttings and by tissue culture at Gensingen, Germany, has shown that the unique features of this new Osteospermum are stable and reproduced true to type in successive generations.

SUMMARY OF THE INVENTION

The following traits have been repeatedly observed and are determined to be the unique characteristics of 'Sirius'. These characteristics in combination distinguish 'Sirius' as a new and distinct cultivar:

1. Mostly upright and bushy plant habit.

2. Freely branching and vigorous.

3. Early and continuous flowering.

4. Large inflorescences with intense dark purple ray florets.

5. Good summer performance, flowering continues through summer.

Plants of the new Osteospermum can be compared to plants of the *Osteospermum ecklonis* cultivar Cape Daisy Lusaka, disclosed in U.S. Plant Pat. No. 10,337. However, in side-by-side comparisons conducted in Gensingen, Germany, plants of the new cultivar differ from plants of the cultivar Cape Daisy Lusaka, in the following characteristics:

1. Plants of the new Osteospermum are more compact than plants of the cultivar Cape Daisy Lusaka.

2. Plants of the new Osteospermum have smaller leaves than plants of the cultivar Cape Daisy Lusaka.

3. Ray floret color of the new Osteospermum is much more intense than ray floret color of the cultivar Cape Daisy Lusaka.

The cultivar Sirius has not been observed under all possible environmental conditions. The phenotype may vary somewhat with variations in environment such as temperature, daylength and light intensity, without, however, any variance in genotype.

BRIEF DESCRIPTION OF THE PHOTOGRAPHS

The accompanying colored photographs illustrate the overall appearance of the new cultivar, showing the colors as true as it is reasonably possible to obtain in colored reproductions of this type.

The photograph at the top of the sheet comprises a top perspective view of a typical flowering plant of 'Sirius'.

The photograph at the bottom of the sheet is a close-up view of typical leaves and lower and upper surfaces of typical inflorescences of 'Sirius'. Foliage and floret colors in the photographs may appear different from the actual colors due to light reflectance.

DETAILED BOTANICAL DESCRIPTION

The following observations, measurements and values describe plants of the new cultivar grown with three plants in a 25.5-cm container in Bonsall, Calif., under outdoor, full-sun conditions with day temperatures ranging from 18 to 35° C. and night temperatures ranging from 13 to 18° C. Plants were pinched (terminal apex removed) one time about two weeks after planting rooted cuttings. Plants used for this description were grown for about 8 to 12 weeks after planting rooted cuttings.

Color references are made to The Royal Horticultural Society Colour Chart except where general terms of ordinary dictionary significance are used.

Botanical classification: *Osteospermum ecklonis* cultivar Sirius.

Parentage:

*Female, or seed, parent.*—*Osteospermum ecklonis* cultivar Sunny Lady, disclosed in U.S. Plant Pat. No. 10,353.

*Male, or pollen, parent.*—Unnamed proprietary selection of *Osteospermum ecklonis.*

Propagation:

*Type.*—By terminal cuttings.

*Time to initiate roots.*—Summer: About 20 days at 22° C. Winter: About 23 days at 20° C.

*Time to develop roots.*—Summer: About 25 days at 22° C. Winter: About 28 days at 20° C.

*Rooting habit.*—Fibrous and freely branching.

Plant description:

*Appearance.*—Perennial herbaceous container and garden plant. Inverted triangle. Mostly upright and bushy growth habit. Freely branching with about 4 or 5 lateral branches.

*Vigor.*—Moderate to vigorous.

*Plant height.*—About 29 cm.

*Plant spread.*—About 25 cm.

*Lateral branch description.*—Length: About 26 cm. Diameter: About 5 mm. Internode length: About 6 mm. Texture: Very sparse short hairs; somewhat succulent. Color: 145B/145C.

*Foliage description.*—Leaves alternate, single. Quantity of leaves: Numerous, about 40 per lateral branch. Length, fully expanded leaves, basal: About 8 cm. Width, fully expanded leaves, basal: About 2.8 cm. Shape: Elliptic. Apex: Broadly acute. Base: Attenuate. Margin: Nearly entire with widely-spaced irregular teeth. Aspect: Mostly flat. Texture: Tough; somewhat granular. Color: Young foliage, upper surface: 146B. Young foliage, lower surface: 146C. Fully expanded foliage, upper surface: 146A. Fully expanded foliage, lower surface: 146B. Attenuated leaf base: 143B. Venation, upper and lower surfaces: 146C.

Inflorescence description:

*Appearance.*—Daisy-type composite inflorescence form; actinomorphic. Disc and ray florets arranged acropetally on a capitulum. Inflorescences displayed above and beyond foliage; about threee per peduncle with about ten opened and unopened inflorescences per plant; peduncles arising from leaf axils. Inflorescences last about one week. Inflorescences persistent.

*Flowering response.*—Plants flower continuously from April to October in the Northern Hemisphere.

*Fragrance.*—Not detected.

*Inflorescence size.*—Diameter: About 7 cm. Depth (height): About 2.5 to 3 cm. Diameter of disc: About 1 cm.

*Inflorescence buds.*—Length: About 1.4 cm. Width: About 7 mm. Shape: Ovoid. Color: 79B to 79C.

*Ray florets.*—Length: About 3.5 cm. Width: About 8 mm. Shape: Ligulate. Apex: Very slightly tri-dentate, minute teeth. Base: Attenuate. Margin: Entire. Aspect: Flat; angled upright, about 135° to peduncle. Texture: Smooth, satiny. Number of ray florets per inflorescence: About 17 in a single whorl. Color: When opening, upper surface: 77A. When opening, lower surface: 79C. Fully opened, upper surface: 78A with darker purple, 83B, longitudinal stripes. Fully opened, lower surface: 79C with darker purple, 83C, longitudinal stripes.

*Disc florets.*—Shape: Tubular; slightly salverform; five-lobed, fluted at apex. Number of disc florets per inflorescence: Numerous, about 48. Length: About 8 mm. Width: About 2 mm. Color: Immature: 91B; apex, 91A. Mature: 91A.

*Phyllaries.*—Shape: Linear. Apex: Narrowly acute. Margin: Entire. Quantity and arrangement: About 17 per inflorescence; whorled. Texture: Coarse. Color: Upper surface: 138A. Lower surface: 137A.

*Peduncle.*—Length: About 6.5 cm. Aspect: Moderately strong; inflorescnces held above and beyond foliage. Texture: Coarse; slightly granular. Color: 144C.

*Reproductive organs.*—Androecium: Present on disc florets only. Stamens: Five; fused. Anther shape: Oblong. Anther size: About 0.1 mm. Anther color: 99A. Pollen amount: Scarce. Pollen color: 14A. Gynoecium: Present on ray and disc florets. Pistils: One. Pistil length: About 5 mm. Stigma shape: Bipartate. Stigma color: 83A. Style length: About 4 mm. Style color: 83B. Ovary color: 155A. Seed: Seed development has not been observed.

Disease resistance: Resistance to pathogens common to Osteospermum has not been observed on plants of the new Osteospermum.

Heat tolerance: Plants of the new Osteospermum have demonstrated good tolerance to high temperatures and exhibited good summer performance.

It is claimed:

1. A new and distinct cultivar of Osteospermum plant named 'Sirius', as illustrated and described.

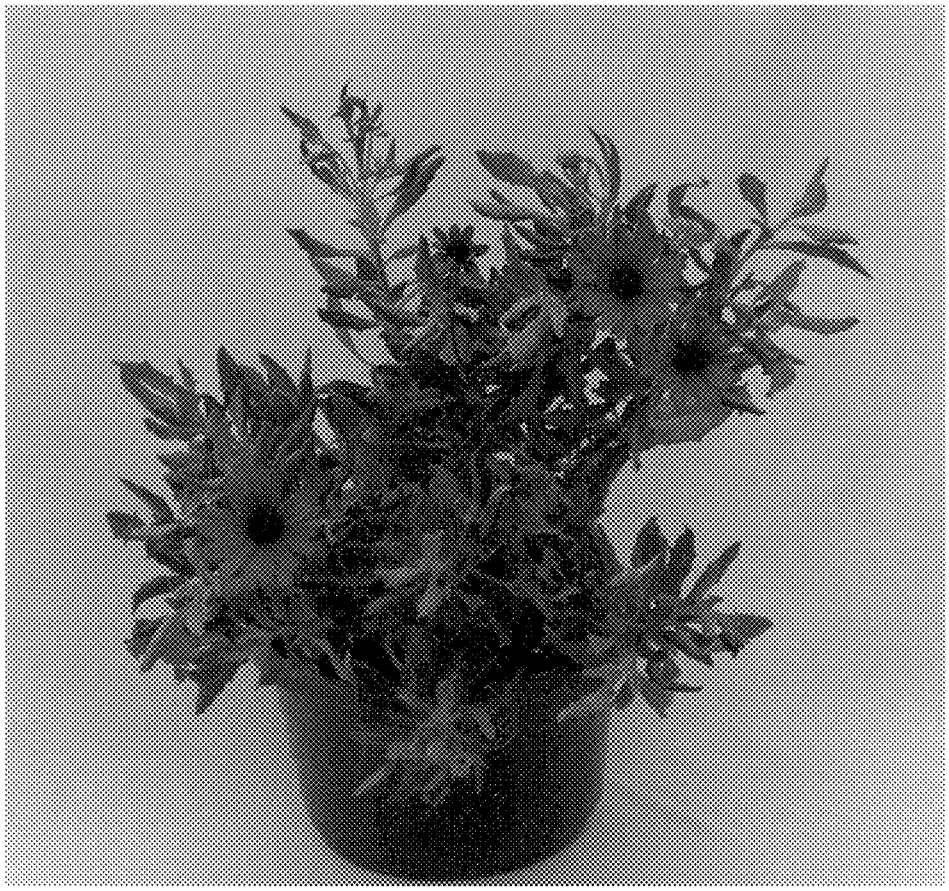
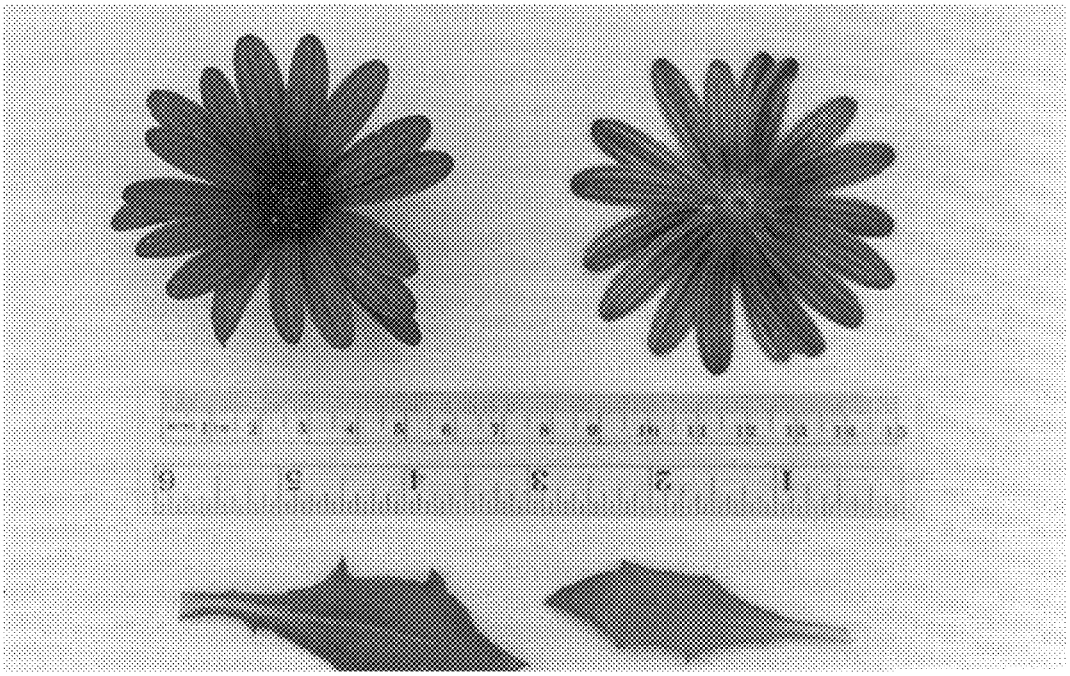

* * * * *